United States Patent

Wimmer et al.

Patent Number: 6,025,510
Date of Patent: Feb. 15, 2000

[54] PROCESS FOR STABILIZING AND DISPERSING VEGETABLE OILS WHICH CONTAIN POLYUNSATURATED FATTY ACID RADICALS BY MEANS OF γ-CYCLODEXTRIN

[75] Inventors: Thomas Wimmer, Marktl/Inn; Marlies Regiert, München; Jens-Peter Moldenhauer, Burghausen, all of Germany

[73] Assignee: Wacker-Chemie GmbH, Munich, Germany

[21] Appl. No.: 09/142,568

[22] PCT Filed: Mar. 27, 1997

[86] PCT No.: PCT/EP97/01581

§ 371 Date: Sep. 15, 1998

§ 102(e) Date: Sep. 15, 1998

[87] PCT Pub. No.: WO97/36972

PCT Pub. Date: Oct. 9, 1997

[30] Foreign Application Priority Data

Mar. 29, 1996 [DE] Germany ............... 196 12 658

[51] Int. Cl.[7] .................................................. C11B 3/02
[52] U.S. Cl. .................. 554/199; 554/198; 554/212; 426/417
[58] Field of Search ............... 424/439; 426/417; 554/198, 199, 212

[56] References Cited

U.S. PATENT DOCUMENTS 4,533,637  8/1985  Yamane et al. .
4,803,077  2/1989  Mitsuhashi et al. .................... 424/439

FOREIGN PATENT DOCUMENTS 0392608  10/1990  European Pat. Off. .
0470452   2/1992  European Pat. Off. .
 470452   2/1992  European Pat. Off. ........ C08B 37/16
2596617  10/1987  France .

OTHER PUBLICATIONS

Chemical Abstract CA:107:22242k, 1987.
Chemical Abstract CA:107 :133049x, 1987.
Chemical Abstract CA:107:22242k, 1987.
Chemical Abstract CA:107:133049x, 1987.
Chemical Abstract CA:87:11647s, 1977.
Chemical Abstract CA:108:220598, 1988.
Chemical Abstract CA:108:192767y, 1988.
Chemical Abstract CA:113:217812, 1990.
Chemical Abstract CA:107:46327t, 1987.
Journal of Inclusion Phenomena and Molecular Recognition in Chemistry 16 (1993), pp. 339–354.
Cyclodextrin Technology; J. Szejtli, Kluwer Academic Publishers, 1988, pp. 87–90 is already.
Journal of Inclusion Phenomena and Molecular Regognition in Chemistry, Bd. 25, Nr. 1, 1996, pp. 213–216, M. Regiert et al.
Database WPI, Derwent Publications Ltd, AN 95–317436 & JP 07 215 911 A (Ensuiko Sugar Refining Co Ltd), 1995.
Yukagaku—Journal of the Japan Oil Chemists' Society, Bd. 41, Nr. 3, 1992, JP pp. 203–206, K. Asakura et al.
Colloids and surfaces a, Bd, 97, Nr. 3, 1995, pp. 263–269, R. Bru et al.
Derwent Abstract (no. 87–3366668 [48]) corresponding to FR 2 596 617, 1987.
Database WPI, Derwent Publications Ltd., AN 87–359752 & JP 62 263 143 A (Kao Corp), 1987.

Primary Examiner—Deborah D Carr
Attorney, Agent, or Firm—Collard & Roe, PC

[57] ABSTRACT

A process is disclosed for stabilizing and dispersing vegetable oils which contain polyunsaturated fatty acid radicals by means of γ-cyclodextrin, as well as the thus obtained complexes and their use. In this process for stabilizing vegetable oils having a high proportion of triacylglycerines and containing polyunsaturated fatty acids, cyclodextrin is mixed with vegetable oil and so a cyclodextrin/vegetable oil complex is formed. This process is characterized in that γ-cyclodextrin is used to form complexes with vegetable oils.

6 Claims, 1 Drawing Sheet

PROCESS FOR STABILIZING AND DISPERSING VEGETABLE OILS WHICH CONTAIN POLYUNSATURATED FATTY ACID RADICALS BY MEANS OF γ-CYCLODEXTRIN

BACKGROUND OF THE INVENTION

1. Field of the Invention

This application is a 371 of PCT/EP97/01581 filed Mar. 27, 1997.

The invention relates to processes for the stabilization and dispersion of vegetable oils comprising polyunsaturated fatty acid radicals by means of γ-cyclo-dextrin, to the complexes thus prepared, and to their use.

2. The Prior Art

Cyclodextrins are cyclic oligosaccharides which consist of 6, 7 or 8 α(1–4)-linked anhydroglucose units. The α-, β- or γ-cyclodextrins, which are prepared by, for example, enzymatic starch conversion, differ in the diameter of their hydrophobic cavity and are generally suitable for the inclusion of a large number of lipophilic substances.

Vegetable oils consist predominantly of simple and mixed triacylglycerols, composed of saturated, monounsaturated or polyunsaturated natural fatty acid radicals with chain lengths of less than or equal to 18 carbon atoms which are esterified with glycerol.

Vegetable oils with a high proportion of triacylglycerols containing polyunsaturated fatty acids are valuable substances whose skin care properties are exploited in cosmetics. In addition, they are employed in the food sector to provide essential fatty acids.

The main problem for the wider use of these oils is their sensitivity to atmospheric oxygen, heat and microorganisms, in particular with exposure to light, peroxides being formed (autoxidation of the unsaturated fatty acid radical). Autoxidation takes place at the C—C double bond, which primarily leads to the formation of peroxides and then to aldehydes, ketones and acids. Secondary reactions involve isomerizations and polymerizations.

The peroxide content, expressed by the peroxide number (PON), is the decisive quality criterion for vegetable oils. Oils with a high peroxide number smell rancid and cannot be used for applications. The peroxide number provides information on the progressive oxidation process, or the amount of lipid peroxides. Changes in color and odor are other characteristics for destabilization of the vegetable oils.

The peroxides formed by destabilization of the unsaturated triacylglyerols increase the undesired toxic potential of the formulations. Also, a series of cosmetically desirable effects are reduced or even eliminated by the destabilization: the following may be mentioned by way of example:

The polyunsaturated fatty acids such as, for example, linoleic acid and gamma-linolenic acid, cause an increased elasticity of the skin by forming mobile and flexible structures in the cell membranes or skin lipids by means of their elbow configuration (C—C double bonds with cis configuration). A high proportion of poly-unsaturated fatty acids leads to a higher packing density of the skin lipids, and this results in an improved barrier function of the skin, which, in turn, leads to reduced transepidermal water loss. Cell proliferation is increased. Autoxidation lowers the number of C—C double bonds and thus the number of the structures responsible for mobility and flexibility.

Apart from the use of oils containing unsaturated triacylglycerols in cosmetics, the topical or oral administration as medicament or as synthetic food may also be mentioned. Certain unsaturated fatty acids such as, for example, linoleic acid or gamma-linolenic acid are absolutely necessary, i.e. esssential, for the mammalian organism since they cannot be synthesized by the latter and must therefore be administered externally.

The following measures are known from the prior art to stabilize, by means of cyclodextrin, vegetable oils containing polyunsaturated fatty acids:

CA:107:22242k describes a cholesterol-lowering foodstuff in which γ-linolenic acid is formulated with α-cyclodextrin.

Milk or powdered milk containing β-cyclodextrin complexes of triacylglycerols with a proportion of 70% of γ-linolenic acid are known from CA:107:133049x.

CA:87:116647s describes cyclodextrin inclusion compounds of α- and β-cyclodextrin with mono-, di- and triacylglycerols exemplified by soybean oil.

In CA:108:220598, it is found that storage of a triacylglycerol/β-cyclodextrin complex at 40° C. for one month results in an over 50% reduced peroxide formation in comparison with non-complexed triacylglycerol.

Chemical Abstract CA:108:192767y describes the stabilization of γ-linolenic acid in evening primrose oil by inclusion into β-cyclodextrin.

In CA:113:217812, β-cyclodextrin is employed for improving the emulsion properties of fatty acids in skin cosmetic formulations.

Chemical Abstract CA: 107:46327t describes therapeutic beverages which comprise a β-cyclodextrin complex of γ-linolenic acid.

Journal of Inclusion Phenomena and Molecular Recognition in Chemistry 16 (1993), pp. 339–354, proves the stabilization of linseed oil as α- and β-cyclodextrin complexes in comparison with free oil by the uptake of oxygen in a Warburg apparatus. The use of α-cyclodextrin is disclosed as being especially preferred in this publication. The authors suggest on p. 342, 3rd paragraph from the bottom, that the linear fatty acids, both free and in the form of their glycerol esters, form the most stable complexes with α-cyclodextrin, which is the cyclodextrin with the smallest cavity.

SUMMARY OF THE INVENTION

It is an object of the invention to provide a method which allows vegetable oils with a high proportion of triacylglycerols comprising polyunsaturated fatty acids to be stabilized against oxidative degradation.

It was another object of the invention to provide a method which allows vegetable oils to be dispersed in aqueous media.

The objects are achieved by a method in which cyclodextrin is mixed with vegetable oil, thus forming a CD/vegetable oil complex, which comprises the use of γ-cyclodextrin for complexation of the vegetable oils.

The use of γ-cyclodextrin allows better stabilization of the vegetable oils than the use of α- or β-cyclodextrin.

No document of the prior art describes the use of γ-cyclodextrin for the complexation, dispersion or stabilization of vegetable oils. As already mentioned, the Journal of Inclusion Phenomena and Molecular Recognition in Chemistry 16 (1993), pp. 339–354, suggests the use of α-cyclodextrin for such purposes. This teaching of the preferred use of the cyclodextrin with the smallest cavity rather diverts a skilled person from the teaching according to the invention, i.e. the use of the cyclodextrin with the largest cavity.

Inclusion of the vegetable oils within γ-CD allows outstanding dispersion of the vegetable oils in water or aqueous solutions.

Vegetable oils with a high proportion of triacylglycerols comprising polyunsaturated fatty acids are defined by the content of, for example, linoleic or α-and γ-linolenic acid. Examples of such vegetable oils are: wheatgerm oil, borage oil, evening primrose oil, blackcurrant oil, linseed oil, sunflower oil, nut oils (almond, peanut), olive oil.

The method according to the invention is especially suitable for stabilizing and dispersing plant oils with a polyunsaturated fatty acid content of >50%.

The composition of the fatty acids of the triacylglycerols can be determined in a known manner by gas chromatographic analysis of the corresponding methyl esters.

The vegetable oils are obtained in a manner known per se, for example by pressing, distillation or extraction with an organic solvent. Typical fatty acid profiles can be seen from the table which follows:

TABLE 1

| Fatty acid | Evening primrose oil | Borage oil | Blackcurrant oil |
| --- | --- | --- | --- |
| Palmitic acid | 6–10% | 9–13% | 6% |
| Stearic acid | 1.5–3.5% | 3–5% | 1% |
| Oleic acid | 6–12% | 15–17% | 10–12% |
| Linoleic acid | 74.2% | 40.4% | 48% |
| Linolenic acid | 8–12% | 19–25% | 30% |
| Others | <1% | <4% | <3% |

Surprisingly, it emerged that vegetable oils can be stabilized, and also dispersed, in an outstanding manner by complexation with γ-cyclodextrin. A markedly higher stabilization of the unsaturated compounds was found in comparison with α- and β-cyclodextrin. When stored under atmospheric oxygen (Example 3), the peroxide numbers of the γ-CD formulation were lower than those obtained with α- and β-CD.

The invention therefore also relates to complexes of γ-CD and vegetable oils with a high proportion of triacylglycerol comprising polyunsaturated fatty acids.

Complexation of the vegetable oils with γ-CD gives unexpectedly stable dispersions in aqueous systems. The preferred particle size of the complexes is approx. 10–100 μm.

The oil-to-water ratio in these dispersions is preferably less than 1 (oil-in-water emulsion).

The invention therefore also relates to oil-in-water emulsions of vegetable oil/γ-CD complexes in aqueous systems.

The complexes of the vegetable oils with γ-CD can be prepared in a manner known per se. This can be effected, for example, from solution, from suspension using the paste method or the kneading method (Cyclodextrin Technology; J. Szejtli, Kluwer Academic Publishers, 1988, pp. 87–90).

Preparation from concentrated aqueous γ-CD solutions has proved advantageous. To this end, the vegetable oil is added to the aqueous γ-CD solution. The CD concentration of the aqueous solution (before the addition of vegetable oil) is preferably between 5 and 50% by weight. A CD concentration of 20–50% by weight is especially preferred.

The weight ratio of vegetable oil to CD is preferably between 1:20 and 1:0.3, especially preferably between 1:10 and 1:0.5.

Vegetable oil and γ-CD/γ-CD solution are mixed either batchwise or continuously.

The batches are mixed vigorously, i.e. kneaded or stirred vigorously, depending on the consistency.

This is preferably effected in a temperature range from above freezing point to 80° C. The process is especially preferably carried out at 20–60° C., particularly at approx. 30–50° C. The mixing time depends on the temperature and is preferably between one hour and a few days. As a rule, a mixing time of 10 to 30 hours will suffice.

Complexing is preferably effected under atmospheric pressure.

Complexing is preferably effected under a protective gas atmosphere (nitrogen or argon).

The complexes, which are sparingly soluble in water, can be used directly in the form of the reaction mixture. Alternatively, they can be isolated and processed by filtration, centrifugation, drying, grinding, sieving, screening, granulating or tableting to suit the procedure which is customary in each case.

Other substances may also be added to the γ-cyclodextrin complexes, depending on the intended use, for example in cosmetic formulations. For example, surfactants, detergent additives, care additives, self-tanning additives, thickeners, preservatives, stabilizers, emulsifiers, fragrances, colorants, antioxidants, vitamins, UV filters and silicone oils. The substances may be added during or after complexation.

They are preferably added after complexation.

The use of the complexes according to the invention of vegetable oils with triacyglycerols comprising polyunsaturated fatty acids leads to homogeneous cosmetic or pharmaceutical preparations of the O/W emulsion type which are storage-stable over a prolonged period, do not separate and have an advantageously high and at the same time constant viscosity.

The complexes or dispersions according to the invention can be used, for example, in cosmetic preparations of bath products (salt, shower products and bubble baths), cosmetic dispersions (creams, masks, emulsions, powders, deodorants), decorative cosmetics (make-up, powders, lipstick bases), sunscreen products, hair care products (shampoo, rinse, hair pack), repellents or soaps.

BRIEF DESCRIPTION OF THE DRAWINGS

In curve 1.

Figure 1:
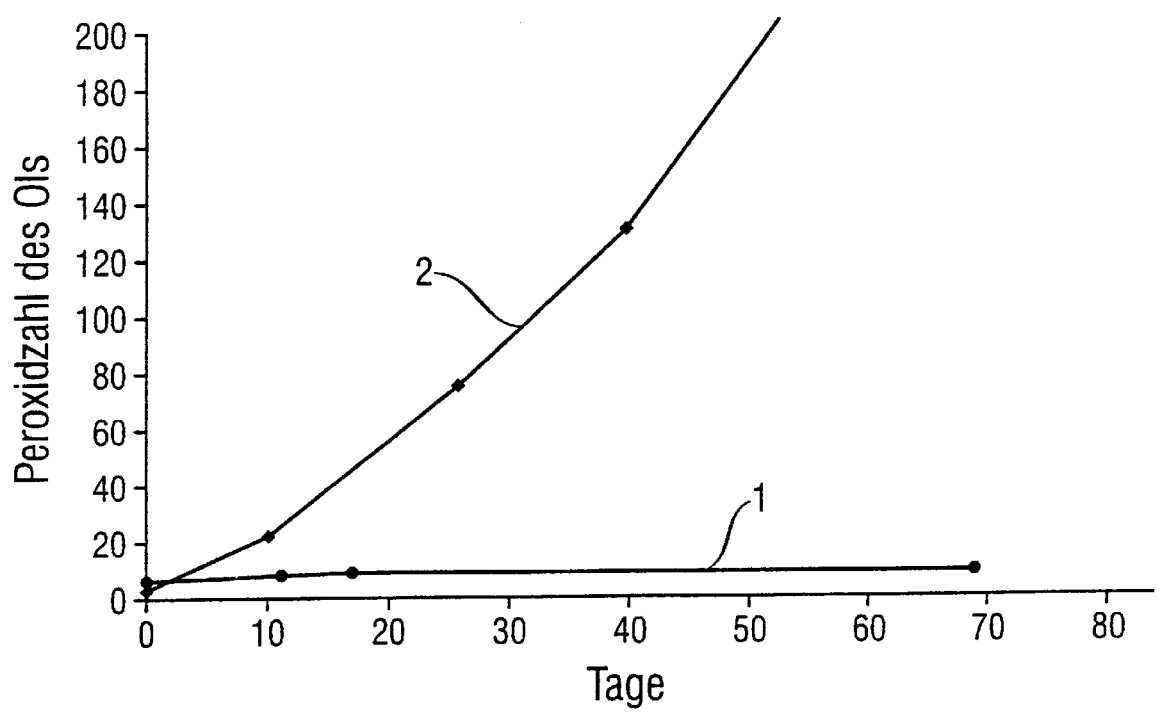
FIG. 1 shows the peroxide number of the γ-cyclodextrin complex of Ex. 5a. Curve 2 shows the increase in peroxide number of the starch trituration of Ex. 5b.

The examples which follow are intended to illustrate the invention in greater detail.

DETAILED DESCRIPTION OF PREFERRED EMBODIMENT

EXAMPLE 1

Complexation of Evening Primrose Oil with α-, β-, γ-CD a) 69.5 g of α-CD were stirred with 162 ml of distilled water, and the mixture was heated to 95° C. and cooled under nitrogen to 45° C. 20.0 g of evening primrose oil (PON=2.9) were added at this temperature and the batch was stirred for 24 hours. After cooling to room temperature, the resulting complex was filtered off with suction and dried in vacuo.

b) 81.1 g of β-CD were stirred with 189 ml of distilled water, and the mixture was heated to 95° C. and cooled under nitrogen to 45° C. 20.0 g of evening primrose oil (PON=2.9) were added at this temperature and the batch was stirred for 24 hours. After cooling to room temperature, the complex was isolated by freeze-drying.

c) In a thermostated flanged vessel, 833.8 g of γ-CD were stirred with 1945 ml of distilled water, and the mixture was heated to 90° C. and cooled under nitrogen to 45° C. At this temperature, 180.0 g of evening primrose oil (PON=2.9) were added and the batch was stirred for 30 hours. After cooling to room temperature, the resulting complex was filtered off by suction and dried in vacuo.

Table 2 shows the composition of the complexes in accordance with Example 1.

TABLE 2

| Complex | Yield [g] | Oil Content [%] | PON directly after complexing | Loss on drying [%] |
|---|---|---|---|---|
| 1a) | 40.5 | 36.3 | 3.1 | 3.4 |
| 1b) | 102.7 | 20.0 | 4.2 | 11.2 |
| 1c) | 802.1 | 22.6 | 3.7 | 10.5 |

EXAMPLE 2

Determination of the Peroxide Number of the Oil Included in Cyclodextrins

To decomplex the evening primrose oil/cyclodextrin complex (of Examples 1a–c), in each case 5 g –10 g of complex were stirred for one hour at room temperature in a mixture of 90 ml of methanol and 60 ml of petroleum ether. The undissolved cyclodextrin was separated off by filtration and the free oil was isolated by distilling off the solvent in vacuo at not more than 30° C. The peroxide number was determined on the resulting oil by iodometric titration following the procedure of DAB [German Pharmacopeial]10.

EXAMPLE 3

Determination of the Storage Stability of Evening Primrose Oil as α-, β-, γ-CD complex In each case 50 g of the complexes (Examples 1a–c) of evening primrose oil with α-, β-, γ-CD were filled into shallow Petri dishes and stored at room temperature in daylight (window sill). Prior to measuring the peroxide numbers (analogously to Example 2) of the included oil, the samples were homogenized by stirring since increased oxidation takes place on the surface (yellow coloring). Tables 3 and 4 give the peroxide numbers, appearance and odor after various storage periods. The stabilizing effect, which can be identified on the basis of the low peroxide number, low odor and lack of coloration, is most pronounced in the case of the γ-CD complex.

TABLE 3

Storage for 22 days

| Complex | PON | Appearance | Odor |
|---|---|---|---|
| 1a) | 115 | nearly white | slightly rancid |
| 1b) | 209 | yellow | markedly rancid |
| 1c) | 83 | white | neutral odor |

TABLE 4

Storage for 38 days

| Complex | PON | Appearance | Odor |
|---|---|---|---|
| 1a) | 159 | yellowish | rancid |
| 1b) | 251 | intense yellow | highly rancid |
| 1c) | 113 | white | nearly neutral odor |

EXAMPLE 4

Complexation of Wheatgerm Oil with γ-CD 657.9 g of dry γ-CD were dissolved in 3000 ml of distilled water at 40° C. 355 g of wheatgerm oil were subsequently added in portions in the course of 50 minutes. Stirring of the batch was continued for 8 hours at 40° C. and for 64 hours at 25° C. The resulting complex was then filtered off and the product was dried in vacuo at 35° C.

EXAMPLE 5

Comparison of a γ-CD Complex with a Starch Trituration of Evening Primrose Oil

5a: 100 g of γ-CD were dissolved in 200 ml of distilled water at 50° C. After 5 g of evening primrose oil had been added, the reaction mixture was stirred for 16 hours, and the mixture was freeze-dried. Yield:102 g with an oil content of 5%. 5b: In a mortar, 100 g of potato starch were triturated thoroughly with 5 g of evening primrose oil until a homogeneous powder with an oil content of approx. 5% was obtained.

50 g each of the γ-CD complex (5a) and of the starch trituration (5b) were filled into Petri dishes and stored in a drying oven at 37° C. At time intervals of a few days to weeks, samples of approx. 10 g of the substances 5a and 5b were taken, and the peroxide number of the evening primrose oil was determined as described in Example 2.

As shown in FIG. 1, inclusion of the oil in γ-cyclodextrin resulted in a very good stabilization of the former over a period of several weeks, while, in comparison, autoxidation of the oil in the starch trituration progresses with increasing time.

EXAMPLE 6

Complexation of Borage Oil with γ-CD

A solution of 80.0 g of γ-CD in 200 ml of distilled water was treated with 17.3 g of borage oil at 40° C. in the course of 2–3 minutes. After the mixture had been blended intimately for 30 minutes using a disperser (Ultra-Turrax), the mixture was stirred for 24 hours at 40° C. and then for 12 hours at room temperature and the complex which precipitated was filtered off. The yield amounted to 81.7 g, with a moisture content of 6.5%. The oil content was 19.4%, based on dry matter.

EXAMPLE 7

Complexation of Blackcurrant Oil with γ-CD 104.3 g of γ-CD were dissolved in 130 ml of distilled water with heating to 95° C., and the solution was cooled to 40° C. under nitrogen. At this temperature, 22.5 g of blackcurrant oil were added, and the pasty batch was kneaded for 20 hours in a planetary mixer. The paste was dried in a vacuum drying oven at 350° C. under a pressure of 1–3 mm Hg. The dried complex was subsequently comminuted in a laboratory mixer and sieved with a sieve of mesh size 200 μm. The yield amounted to 118 g, with a PON of 7.4. No rancid odor was observed after storage for two weeks at room temperature.

EXAMPLE 8

Oil Bubble Bath with Wheatgerm Oil

| | |
|---|---|
| Water | 53 g |
| γ-Cyclodextrin | 16 g |
| Wheatgerm oil | 6 g |
| Coconut fatty alcohol ether sulfate | 23 g |
| Methylparaben | 0.1 g |
| Perfume oil | 1.9 g |

The wheatgerm oil is stirred into the aqueous solution of γ-cyclodextrin at 30° C. while flushing with $N_2$. After the mixture has been stirred for 3 hours, the other components are admixed one after the other, and stirring is continued for 2 hours.

EXAMPLE 9

Moisturizing Lotion with Evening Primrose Oil

| | |
|---|---|
| Water | 62 g |
| γ-Cyclodextrin | 14 g |
| Evening primrose oil | 3 g |
| Siloxane polyglycoside | 13 g |
| Isooctadecyl isononanoate | 2 g |
| White petroleum jelly | 2 g |
| Laureth | 3 g |
| Methylparaben | 0.1 g |
| Perfume oil | 0.9 g |

Preparation:

The evening primrose oil is stirred into the aqueous solution of γ-cyclodextrin at room temperature while flushing with $N_2$. After the mixture has been stirred for 5 hours, the other components are admixed one after the other, and stirring is continued for 2 hours.

EXAMPLE 10

Conditioning Hair Care Shampoo

| | |
|---|---|
| Water | 52 g |
| γ-Cyclodextrin | 8 g |
| Blackcurrant oil | 2 g |
| Sodium lauryl sulfate | 19 g |
| Cocoamidopropylbetaine | 10 g |
| Dimethicone DM 350 | 2 g |
| Cocamide MEA | 6 g |
| Perfume oil | 1 g |

Preparation:

The currant oil is stirred into the aqueous solution of gamma-cyclodextrin at room temperature while flushing with $N_2$. After the mixture has been stirred for 3 hours, the other components are admixed one after the other, and stirring is continued for 80 minutes.

EXAMPLE 11

Mild Refatting Bath Salt

| | |
|---|---|
| Sodium lauryl sulfate | 20 g |
| Sodium sesquicarbonate | 40 g |
| γ-Cyclodextrin complex with evening primrose oil as in Example 1c | 40 g |

The components mentioned are homogenized for 30 minutes in a ball mill.

EXAMPLE 12

Complexation of Sunflower Oil with α-CD 120 g of α-cyclodextrin, dissolved in 650 ml of water, and 220 g of sunflower oil are introduced into a 1000 ml glass flask. The mixture is stirred for 24 hours at 40° C. using a KPG stirrer. This gives a very fine dispersion of the oil in water. Observation: The viscosity (Brookfield viscometer: 10 rpm; spindle S2, viscosity 310 mPas) of the emulsion remains unchanged when stored at 25° C. over 5 days.

After approx. 14 days, phase separation can be observed.

EXAMPLE 13

Complexation of Sunflower Oil with β-CD

The procedure was as in Example 12, except that 120 g of β-cyclodextrin were used. Observation: At the beginning, a fine oil-in-water dispersion is formed. The viscosity (Brookfield, as in 1a) increases only slightly from 100 mPas to 500 mPas in the course of 14 days.

EXAMPLE 14

Complexation of Sunflower Oil with γ-CD

The procedure is as in Example 12, except that 120 g of γ-cyclodextrin are used. Observation: A stable oil-in-water emulsion is formed. The viscosity (initial value: 350 mPas) increases greatly to a cream-like consistency in the course of 14 days (viscosity: 25000 mpas). No phase separation is observed even after 4 weeks.

We claim:

1. A method for dispersing a vegetable oil in an aqueous medium comprising the steps of
   providing a vegetable oil with a high proportion of triacylglycerols comprising a reaction product of glycerol with polyunsaturated fatty acids;
   reacting said vegetable oil with γ-cyclodextrin to form a γ-cyclodextrin/vegetable oil complex; and
   dispersing said γ-cyclodextrin/vegetable oil complex in an aqueous medium.

2. The method as claimed in claim 1, wherein the weight ratio of vegetable oil to γ-cyclodextrin is between 1:10 and 1:0.5.

3. The method as claimed in claim 1, wherein complex formation is effected in a temperature range from above freezing point to 80° C.

4. The method as claimed in claim 1, wherein a mixing time is used and is between one hour and several days.

5. The method as claimed in claim 1, wherein complexation is effected under a protective gas atmosphere.

6. The method as claimed in claim 5, wherein the protective gas atmosphere is selected from the group consisting of nitrogen and argon.

* * * * *